US006685684B1

(12) United States Patent
Falconer

(10) Patent No.: US 6,685,684 B1
(45) Date of Patent: Feb. 3, 2004

(54) POUCH FOR COLLECTING MATTER EXCRETED BY THE BODY

(75) Inventor: Malcolm Ian Falconer, London (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 85 days.

(21) Appl. No.: 09/613,259

(22) Filed: Jul. 10, 2000

(30) Foreign Application Priority Data

Jul. 13, 1999 (GB) .............................................. 9916342
Jul. 20, 1999 (GB) .............................................. 9917019

(51) Int. Cl.[7] .................................................. A61F 5/44
(52) U.S. Cl. ...................................... 604/355; 604/332
(58) Field of Search .................................... 604/333, 334, 604/335, 336, 337, 338, 339, 332, 340–353, 355

(56) References Cited

U.S. PATENT DOCUMENTS

| 4,886,509 A | * | 12/1989 | Mattsson | 604/349 |
|---|---|---|---|---|
| 5,695,485 A | * | 12/1997 | Duperret et al. | 604/349 |
| 5,702,381 A | * | 12/1997 | Cottenden | 604/385.01 |
| 6,054,631 A | * | 4/2000 | Gent | 156/219 |
| 6,186,990 B1 | * | 2/2001 | Chen et al. | 4/451 |
| 6,338,729 B1 | * | 1/2002 | Wada et al. | 604/385.09 |
| 6,416,500 B1 | * | 7/2002 | Wada et al. | 604/349 |
| 6,530,909 B1 | * | 3/2003 | Nozaki et al. | 604/349 |

FOREIGN PATENT DOCUMENTS

| EP | 0 815 812 | * | 1/1998 |
| GB | 2 268 882 | * | 1/1994 |
| GB | 2 301 350 A | * | 12/1996 |
| GB | 2 329 339 A | * | 3/1999 |
| GB | 2 351 238 A | * | 12/2000 |

* cited by examiner

Primary Examiner—Weilun Lo
Assistant Examiner—Michael Bogart
(74) Attorney, Agent, or Firm—Stuart E. Krieger

(57) ABSTRACT

A pouch includes a front wall (22), a rear wall (24) having an entrance aperture (32), and a central partition (36). The partition divides the pouch into an entrance chamber (38) and a collection chamber (40) located one in front of the other. A pad (42) of superabsorbent material is located in the collection chamber (40) and extends above the lower level of the entrance aperture (32). In use, urine entering the pouch is directed downwardly and through a lower permeable region (36) of the partition, whereafter it is absorbed and gelled by the superabsorbent material pad. The urine is also wicked upwardly by the pad (42) so that the full height of the pouch can be used as a liquid-collection region.

21 Claims, 5 Drawing Sheets

POUCH FOR COLLECTING MATTER EXCRETED BY THE BODY

FIELD OF THE INVENTION

This invention relates to a pouch for collecting matter excreted by the body, in particular for collecting excreted liquid. In one aspect, the invention relates to a urine collection pouch, for example, a urostomy pouch or an urine incontinence pouch such as a leg bag. In one form, the pouch is a so-called ventless pouch (i.e. without any dedicated vent for venting gas, such as flatus gas).

DESCRIPTION OF PRIOR ART

Many different designs of urostomy pouch are known. FIG. 1 illustrates schematically an example of a known design of urostomy pouch 10 in common use. The pouch comprises material defining a front wall 11 and rear wall 12 welded together around at least a portion of their common periphery. An entrance aperture 13 is formed in the rear wall 12 towards the upper region of the pouch 10, and a bag-side coupling member 14 is welded around the aperture 13 for releasable fastening to a body-side pad or wafer (not shown) worn on the body.

A urostomy pouch typically does not require any gas vent because the matter entering the pouch is purely liquid (i.e. urine), rather than a mixture of slurry and gas (flatus). Such pouches are therefore "filterless" and "ventless" and do not require the added complexity and expense of a flatus filter and vent, or a liquid/gas separator member.

In use, urine enters the pouch through the aperture 13, and collects in the bottom of the pouch. As more urine is collected, the liquid level in the pouch rises until it approaches the lower edge or point 15 of the entrance aperture 13. The theoretical capacity of the pouch is defined by the level of the edge or point 15; once the liquid exceeds that level, it will tend to overflow back out of the aperture 13 against the wearer's stoma. In practice, a non-return valve 16 is normally used just below the aperture 13 (for example as described in GB-A-2 145 334). This serves to prevent urine in the pouch from splashing or leaking out through the aperture 13 as the wearer moves about, or sits or lies in a reclined position. The usable capacity of the pouch is then further restricted to the level 16a of the non-return valve 16.

Such a pouch (and also a method of inserting a superabsorbent sheet through the entrance aperture and non return valve) are also described for example in GB-A-2268882.

Reference is also made to U.S. Pat. No. 5,549,587 which describes an ostomy bag with a flatus filter and having a liquid-gas separation device disposed within the bag. The separator is made of an absorbent material to collect liquids and separate these components from any gas entering the bag through the stomal aperture. The separator is spaced from the bag's filter to further enhance the gas-liquid separation. The separator may be disposed within the bag in an attached or unattached configuration. A perforated wall may be included within the bag to minimize clogging of the separator by solids so as to improve gas-liquid separation. The essence of this patent is to use an absorbent member in a pouch having a gas vent/filter in order to separate the gas and liquid components of the bag contents, and to provide some protection for the filter. However, this teaching is irrelevant for a pouch such as urostomy pouch which does not require a gas filter and vent; the sole motivation for the separator design is to address the problem of liquid-gas separation for the vent (whether or not a filter is provided).

SUMMARY OF THE INVENTION

It would be desirable, in one aspect, to increase the usable capacity of the pouch relative to the interior volume of the pouch, especially for a liquid collection pouch.

In contrast to the above prior art design, one aspect of the present invention is to provide, in a pouch comprising first and second walls with an entrance aperture in the first wall, means extending above the lower level of the entrance aperture for collecting liquid in at least a portion of an upper region of the pouch above said lower level of the aperture.

The invention can therefore enable the urine capacity of the pouch to be increased, by making use of the hitherto unavailable upper volume of the pouch (above the lower level of the entrance aperture).

Preferably, the means extending above the lower level of the entrance aperture comprises one or more wicking members capable of drawing liquid upwardly by a wicking effect.

Preferably, the means extending above the lower level of the entrance aperture comprises liquid gelling material. Preferably, the material is a so-called super absorbent material. A suitable super absorbent material is or comprises sodium polyacrylate. In a preferred embodiment, the superabsorbent material is in the form of a laminate, the superabsorbent powder being compressed or bonded between 2 papers, for example tissue paper and/or weldable paper. Such a laminate holds the superabsorbent powder together, enabling it to be handled and cut during manufacture. It also prevents the suderabsorbent from disintegrating inside the pouch in use. This is particularly important if a thin pad is used in the pouch. A further advantage is that, if a weldable paper sheet is used as one of the webs of the laminate, the laminate can be welded to the pouch wall to secure the laminate in position.

Preferably, the super-absorbent laminate material comprises, or is part of a composition which also comprises, glycerol. The glycerol can act as a humectant, to improve the wicking effect in the material, and avoid gel-locking. The composition is preferably as described in GB-A-2301350 or GB-A-2325432.

Preferably, the absorbent material is arranged in the form of one or more pads or other members which retain substantially their integrity when wetted by urine. This can prevent the superabsorbent laminate, or the gel produced when wet, from tending to fall to the bottom of the pouch, which might otherwise reduce the advantage of being able to use the upper region of the pouch as a collection volume. If desired the pad can be attached to a wall of the pouch, for example, by adhesive or welding. This also prevents the pad from tending to drop down in the pouch, and also serves to positively locate the pad during manufacture.

Particularly when the pouch is a urostomy pouch, it is preferred that an intermediate wall be provided between said means (for example an absorbent member), and the entrance aperture. The intermediate wall can serve to screen the aperture from direct communication with said means. Therefore, the wearer's sensitive stoma can be protected from direct contact with, for example, the superabsorbent laminate material, which can otherwise cause irritation of the stoma from prolonged contact. The intermediate wall may extend part-way down the length of the pouch.

Preferably, a non-return system is employed to allow liquid to pass from the entrance aperture towards the absorbent material, but to obstruct matter passing back towards the entrance aperture. The non-return system may, if desired, comprise material with directional flow characteristics, and/or it may rely on liquid being gellified.

In a second broad aspect, the invention provides a pouch comprising walls defining first and second chambers arranged with a portion of one generally horizontally in front of a portion of the other, an entrance aperture communicating with the first chamber, and wherein, in use, liquid entering the pouch through the entrance aperture flows into the first chamber and from the first chamber directly or indirectly into the second chamber, the first chamber acting as an intermediate chamber for the liquid, and the second chamber acting as a collection chamber.

Preferably, the pouch comprises an entrance aperture in a face thereof.

Preferably, the first and second chambers are separated by one or more walls acting as a non-return system to allow liquid in the first chamber to enter the second chamber, but to obstruct matter in the second chamber from passing into the first chamber.

Preferably, the non-return system is effective to prevent liquid in the second chamber from passing back to the first chamber.

Preferably, the one or more walls are made of material which is liquid permeable in one direction, but which obstructs the passage of liquid in the opposite direction. Such material may, for example, include directional pores.

Preferably, the second chamber contains material for gellifying liquid in the second chamber. Preferably the material is an absorbent, such as a super-absorbent.

Preferably, the pouch is a urostomy pouch or an incontinence pouch.

In a third broad aspect, the invention provides a pouch for collecting matter excreted by the body, the pouch having an outer profile consisting substantially of a first upper curved arcuate portion and a second lower arcuate portion, at least one of the arcuate portions having a maximum transverse dimension greater than the transverse dimension at the point where the first and second portions meet.

Such a pouch profile thus defines a form of figure-of-eight shape. The transverse dimensions of the upper and lower portions may be similar, or one of the portions (for example, the lower portion) may have a greater transverse dimension than the other portion.

Such a pouch profile can assist in controlling the extent to which the pouch, in use, will tend to bulge outwardly as the pouch fills. In the prior art, such control has hitherto only been possible by incorporating one or more spot welds to define a quilted arrangement. However, such spot welds result in high stresses in the pouch material surrounding the weld, and in the weld itself; such spot welds have, sometimes, been known to fail.

The region in which one arcuate region joins the other can also act as a form of marker or indicator, to indicate to the user in a highly unambiguous manner, when the pouch is nearly full and will soon require replacement or emptying.

Preferably, the profile has a waist region at the point where the upper and lower arcuate portions meet. Depending on the design of the pouch, the waist may be used to form a non-return valve within the pouch, by virtue of two closely spaced sheets constricted which allow liquid to dribble therebetween, but which tend to prevent splashing back of the liquid.

Preferably, at least one of the upper and lower portions corresponds to an arc of a circle.

Preferably, the pouch comprises an entrance aperture having a centre located generally in register with a centre of curvature of the upper portion.

Preferably, the pouch carries a coupling member welded to the pouch wall in register with the aperture.

In a fourth aspect, the invention provides a pouch for collecting matter excreted by the body, the pouch having a welded seam, the seam defining an interior pouch profile consisting substantially of a first upper curved arcuate portion and a second lower arcuate portion, at least one of the arcuate portions having a maximum transverse dimension greater than the transverse dimension at the point where the first and second portions meet.

In a yet further aspect, the invention provides a pouch consisting generally of material defining a front wall and a rear wall, at least one of the walls having an entrance aperture for allowing material to enter the pouch for collection therein. The pouch may be intended to be disposable when full, or it may be drainable.

In a yet further aspect, the invention provides a urine collection pouch, the pouch comprising first and second walls, an entrance aperture in the first wall for allowing urine into the pouch, and the pouch defining first and second interior chambers, the first chamber being in communication with the aperture, and the second chamber containing an absorbent material.

Preferably, the first chamber acts as an intermediate chamber from which urine flows to the second chamber to interact with the absorbent material.

Preferably, the absorbent material turns the urine liquid to a gel. Preferably, the material is a superabsorbent material.

Preferably, the entrance aperture is in a face of the pouch.

Preferably, the pouch is a urostomy pouch or a urine incontinence pouch.

The above aspects of the invention may either be used independently, or two or more aspects may be used in combination to achieve yet further advantages.

DESCRIPTION OF THE DRAWINGS

Embodiments of the invention are now described, by way of example only, with reference to the accompanying further drawings, in which.

DESCRIPTION OF PREFERRED EMBODIMENTS

Figure 1:
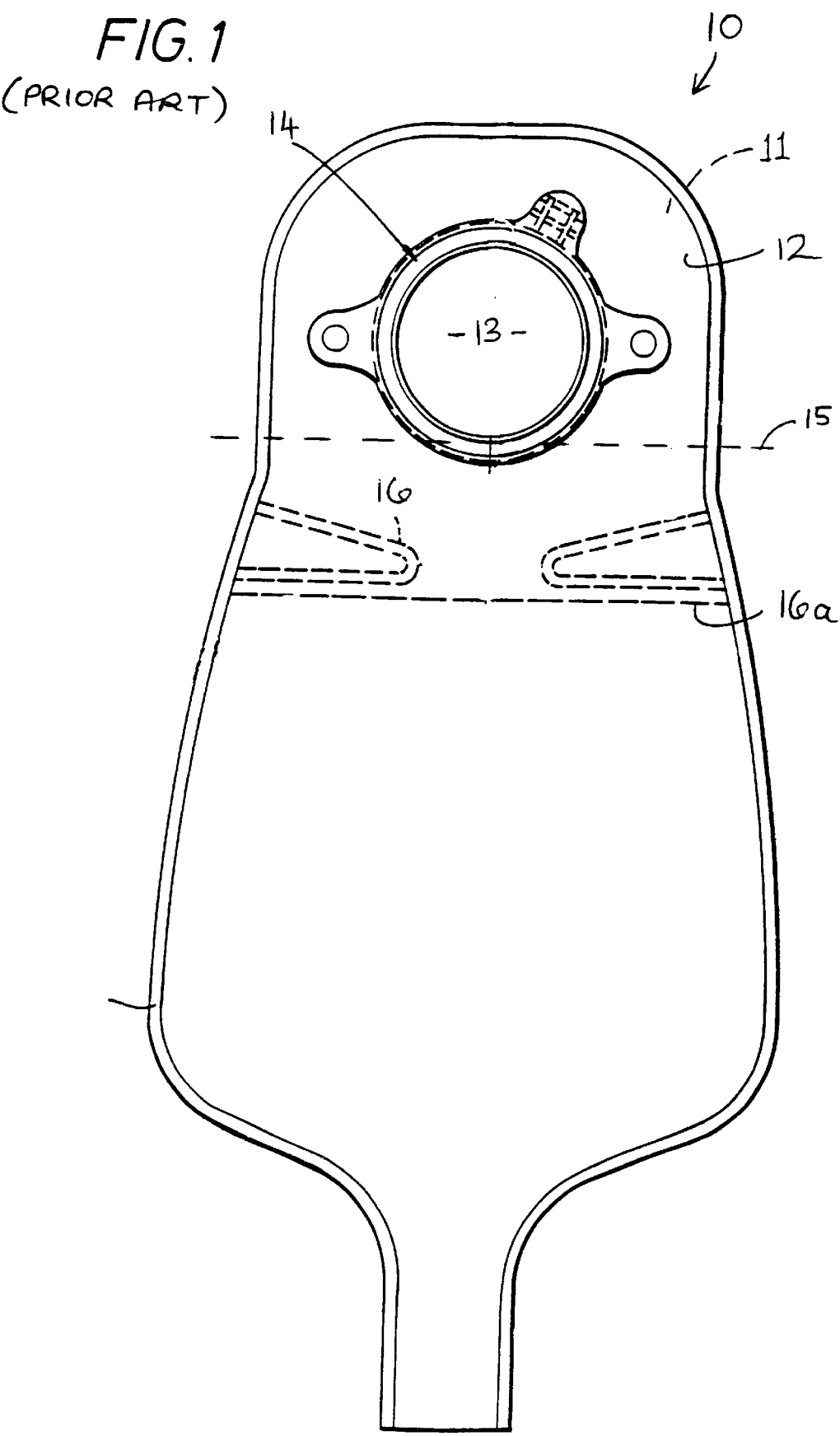
(FIG. 1 is a schematic representation of a prior art pouch)

Referring to FIGS. 2 to 5 of the drawings, a urostomy pouch 20 consists generally of a front wall 22 and a rear wall 24 welded together around their common peripheral seam 26 to define a pouch envelope. The walls 22 and 24 are typically made of a liquid impermeable plastics film laminate, examples of which are well known to the skilled man. A front comfort layer 28 and a rear comfort layer 30 of soft material are positioned outside the front wall 22 and rear wall 24, and sealed thereto along the common seam 26 (to avoid cluttering the drawings the comfort layers are shown only in FIG. 3).

An entrance aperture 32 is provided in the upper region of the rear wall 24, and a coupling member 34 is welded to the pouch in register with the aperture 32. In the present embodiment, the coupling member 34 is intended to form a mechanical interlock with a complementary coupling member (not shown) worn on the body. However, in other embodiments, the coupling member may comprise an adhesive wafer for adhesive attachment directly to the body or to a body-side coupling member.

The interior of the pouch 20 is divided by a partition 36 into an entrance chamber 38 which communicates with the entrance aperture 32 and a collection chamber 40. A pad 42 of or containing superabsorbent material is received in the collection chamber 40, and extends above the lowermost level or point (indicated at 44) of the entrance aperture 32; as illustrated, the pad 42 is of approximately the same height as the interior of the pouch.

A currently preferred composition for the pad 42 is that described in GB-A-2301350, namely comprising superabsorbent (for example, sodium polyacrylate), glycerol and water. The materials are present in parts by weight (pbw):

superabsorbent 100 pbw.

water 0.6 to 6 pbw.

glycerol 5 to 30 pbw.

The glycerol provides significant advantages by acting as a humectant to increase the wicking effect and to avoid gel-locking when the urine contacts the superabsorbent. It also enables the composition to be formed into a self-supporting laminate pad by simply compressing the material between the upper and lower sheets, for example, paper sheets to amalgamate it structurally. The sheets may for example be of tissue paper. One of the sheets might be of plastics weldable paper, to enable the laminate to be secured in position in the pouch during manufacture by welding.

As described in GB 2301350, the composition may also include a food preservative and/or a malodour counteractant, to reduce the chances of unpleasant odours building up in, and escaping from, the urine collected in the pouch.

In the present embodiment, the partition 36 comprises a first intermediate wall 46 of liquid impermeable plastics film, and a second intermediate wall 48 of liquid permeable material. The first and second intermediate walls are positioned one behind the other, and are joined to the front and rear walls of the pouch at the common weld seam 26. The first intermediate wall 46 extends only part-way down the length of the pouch, and serves, in use of the pouch, to direct incoming urine downwardly in the pouch, rather than allowing urine to pass directly to the superabsorbent containing pad 42. The second intermediate wall 48 extends substantially the full length of the pouch. The intermediate walls together prevent the superabsorbent pad 42 from contacting directly the wearer's sensitive stoma. This can provide a degree of security and protection in case the superabsorbent material might irritate the wearer's stoma if in prolonged contact.

It will be appreciated that the intermediate walls thus define a partition 36 with an upper liquid impermeable protection region 50, and a lower liquid permeable region 52. The use of two intermediate walls 46 and 48 as described above has been found to provide a convenient way of constructing the partition, being relatively easy to manufacture using mass production techniques. It will be appreciated that the positions of the walls 46 and 48 may be interchanged, or other structures may be used to form an equivalent partition in this embodiment.

Figure 2:
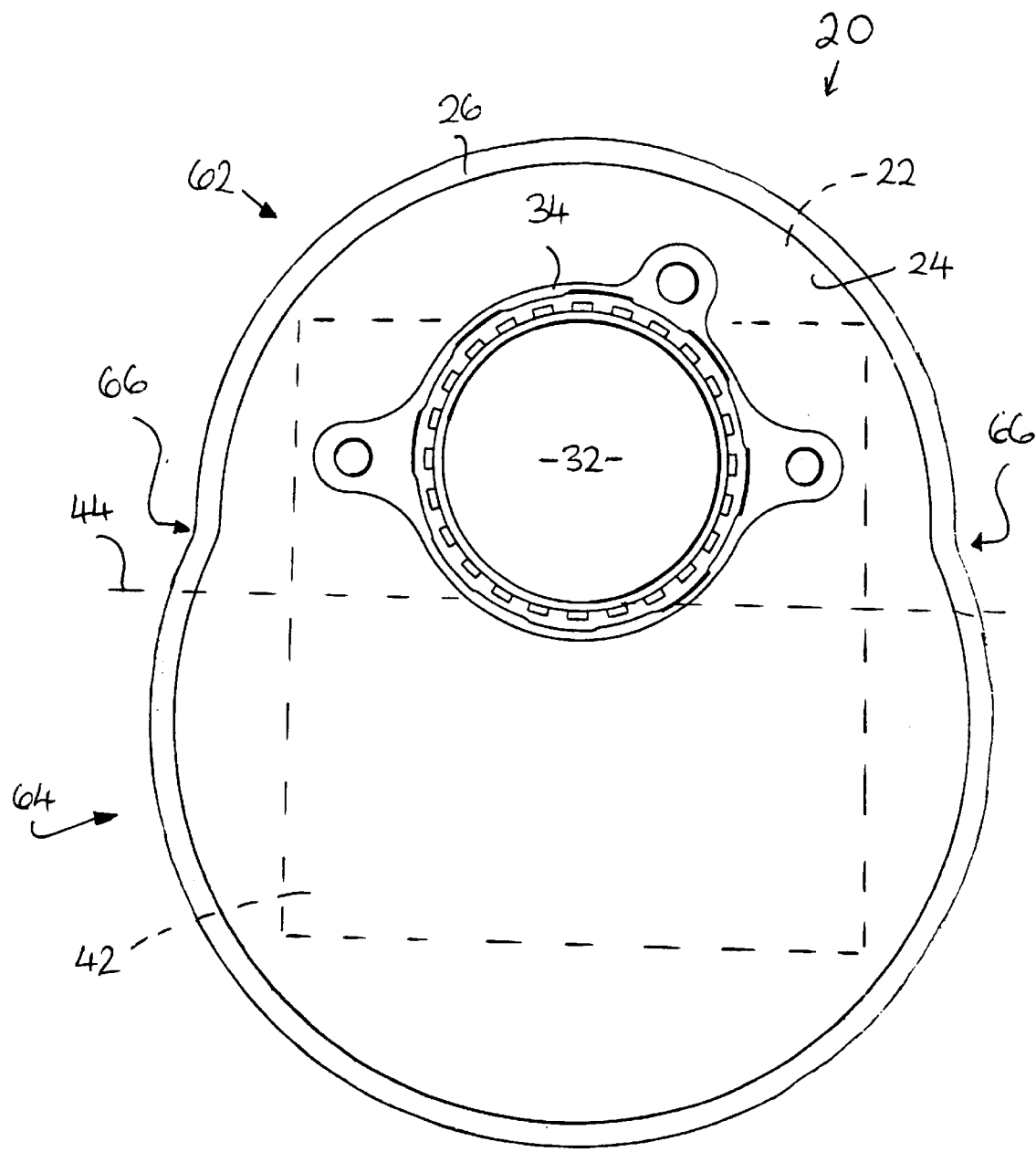
FIG. 2 is a rear view of a urostomy pouch.
Figure 3:
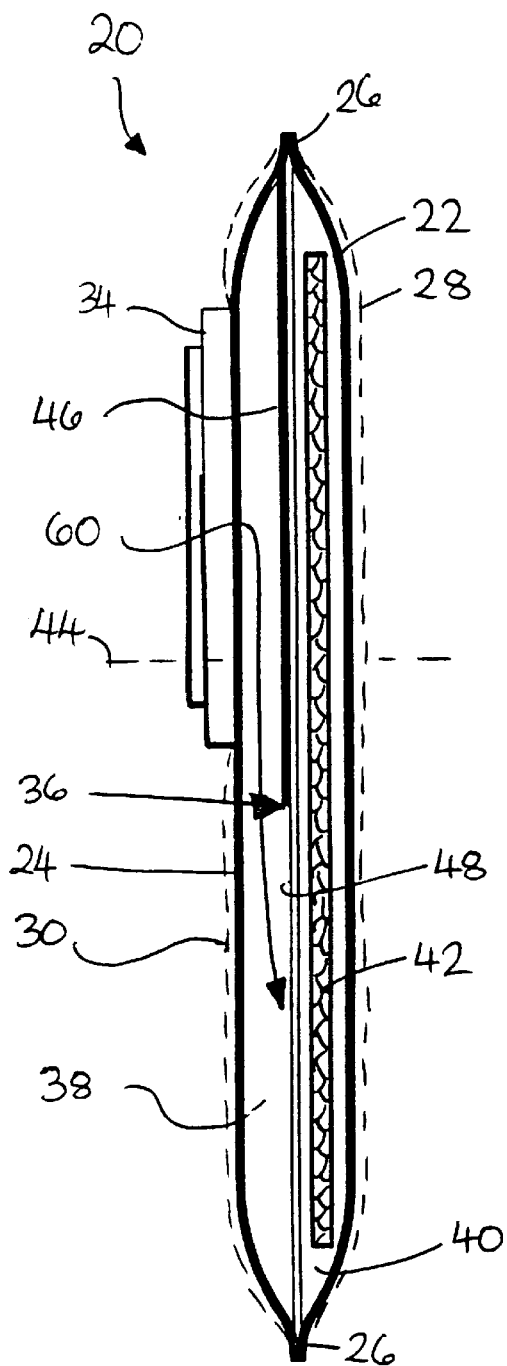
FIG. 3 is a cross section through the pouch showing how urine enters the pouch.
Figure 4:
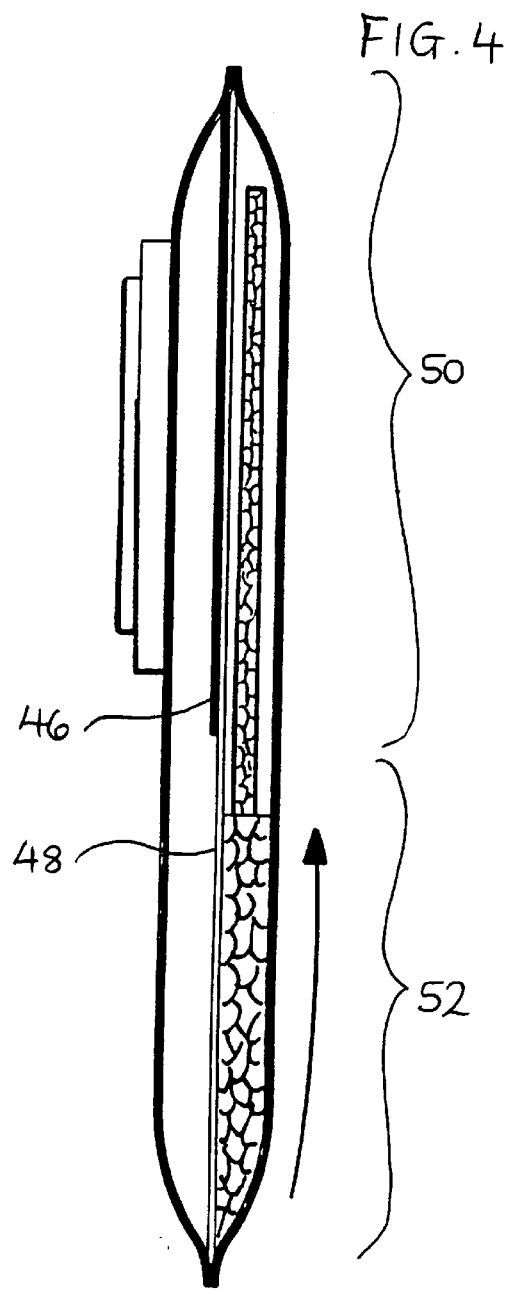
FIG. 4 is a cross-section similar to FIG. 3 showing how urine is collected.
Figure 5:
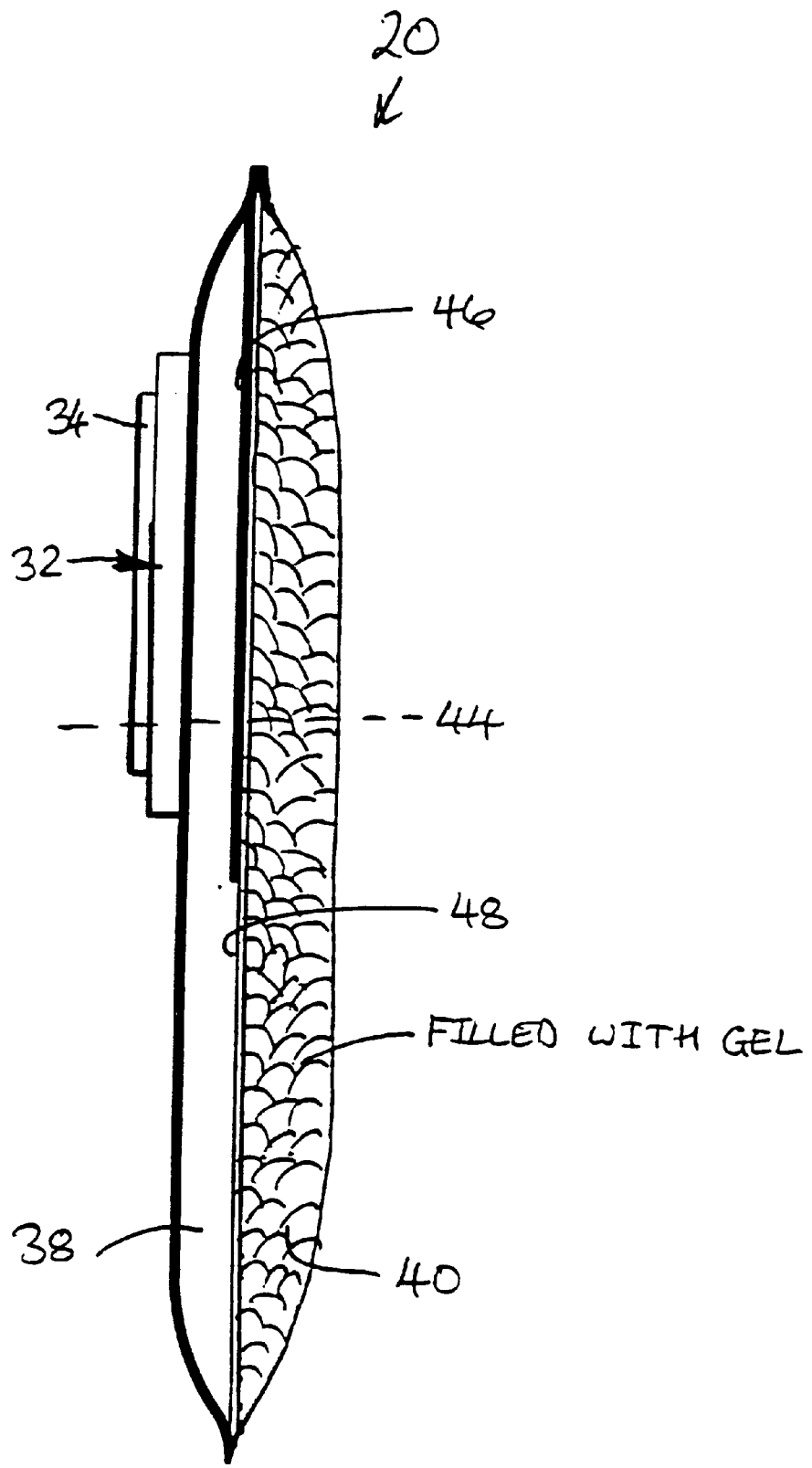
FIG. 5 is a cross section similar to FIG. 4 showing the pouch when almost

In use, urine entering the pouch follows the path indicated by arrow 60 in FIG. 2. The urine does not pass through the impermeable first intermediate wall 46, but instead runs down towards the bottom of the pouch in the entrance chamber 38. Once the urine has passed below the first intermediate wall 46, it is able to pass through the second intermediate wall 48 into the collection chamber 40 where it is soaked up by the superabsorbent pad 42 (FIG. 3). The nature of the superabsorbent material is such that, provided that the pad 42 is in contact with the partition 36, the superabsorbent tends to draw any urine in the entrance chamber 38 through the permeable wall 48 into the pad 42. The urine tends to wick up the pad 42 as it is absorbed, and the superabsorbent material interacts with the urine to form a gel. The superabsorbent material expands as it forms the gel.

By directing the urine downwardly in the entrance chamber 38 before it passes into the collection chamber, there is less chance of excess urine splashing back against the stoma before all the urine is able to pass through the partition 36. Also, the urine gels in the pad 42 from the bottom upwardly, thereby preventing unwanted initial bulging of the pad 42 in the region of the entrance aperture 32. It will be appreciated that such bulging of the pad 42 immediately opposite the entrance aperture might tend to obstruct the aperture.

The pores in the liquid permeable second intermediate wall 48 are such that, although liquid may pass therethrough, the gellified urine is unable to pass back; the gellified urine thus remains trapped in the collection chamber 40. In the present embodiment, the second intermediate wall 48 is made of material having directional pores which permit liquid to flow therethrough in one direction, but obstruct the flow of liquid in the return direction. This is preferred because the superabsorbent laminate material can take a few seconds to absorb the urine, particularly if the urine is discharged into the pouch in relatively large quantities.

The result is that, even if the pouch is subjected to shaking by the wearer's physical movements, or is turned on its side if the wearer sits or reclines, the gellified urine will not tend to leak back into the entrance chamber 38 and escape through the entrance aperture 32. The pouch 20 can therefore provide optimum protection for the wearer.

As more urine is collected and absorbed by the pad 42 (FIGS. 3 and 4), the urine will wick upwardly towards the top of the pad. Since the pad 42 extends above the lowermost point (44) of the aperture 32, this embodiment enables the full height of the pouch to be used for liquid collection. In other words, the region above the level 44 which is unused and wasted volume in previous designs of urostomy pouches, is able to be used as available volume for liquid collection.

In the present embodiment, the amount of superabsorbent in the collection chamber 40 is greater than the amount of superabsorbent required to completely fill the volume of the collection chamber with gel. Therefore, even when the pouch becomes full, the material in the collection chamber 40 remains as gel completely filling the chamber.

It will be appreciated that, for the sake of clarity, the drawings show the pouch walls separated from each other (almost inflated) so that the pouch structure is clear. However, during use of the pouch, the pouch will initially be maintained in a flat configuration. As urine is collected in the collection chamber (40), this chamber will tend to occupy the majority of the volume of the pouch. The entrance chamber 38 will tend to remain generally flat. Therefore, the provision of the entrance chamber 38 does not reduce the effective capacity of the main collection chamber 40.

As best seen in FIG. 2, the pouch is has a figure-of-eight shape, defined by an upper arcuate profile region 62, and a lower arcuate profile region 64 meeting at a slight waist 66. In use, the waist 66 serves to control the extent to which the pouch can bulge, and helps maintain a relatively low (flat) pouch profile, even when the collection chamber 40 is completely filled by gel. The waist therefore assists in holding the pad 42 flat against the partition 36 so that urine will be drawn from the entrance chamber 38 into the collection chamber 40 efficiently.

The upper and lower arcuate profile regions are generally arcs of a circle, and the lower region 64 has a slightly greater lateral dimension (diameter) than the upper region 62. The entrance aperture 32 is positioned generally in register with the centre of curvature of the upper region 62.

It has not been found necessary to fit a separate non-return valve in the present embodiment, because the one-way characteristic of the second intermediate wall 48 and the gellification of the urine in the collection chamber 40 is sufficient to prevent urine from splashing or leaking back through the entrance aperture 32. However, if desired, a one-way valve could be incorporated in the entrance chamber 38 just below the entrance aperture 32. It will be appreciated that the fitting of such a valve would not reduce the capacity of the pouch (a problem suffered in the prior art), because the full pouch height is still available for liquid collection in the collection chamber 40. If desired, the waist 66 could be extended downwardly (i.e. narrowed) to form a non-return type constriction below the entrance aperture 32.

The present embodiment is intended as a disposable, short duration urostomy pouch. The pouch is a little smaller than usual, having an overall height of about 16 cm, and an overall width of about 13 cm. Such a small size of pouch is able to be worn under sports clothing, without being embarrassingly prominent. The small size is made practicable by virtue of at least a portion of the upper region of the pouch being available as a liquid collection volume. Also, since the superabsorbent laminate material acts to gellify the urine, there is no sloshing of the urine inside the pouch; this makes the pouch suitable for use as an activity or sports pouch, enabling the ostomate more easily to engage in activities with much less risk of personal embarrassment.

Although the above embodiment refers to a small urostomy pouch, the same principles may be used to improve the characteristics of larger pouches for any suitable use.

Figure 6:
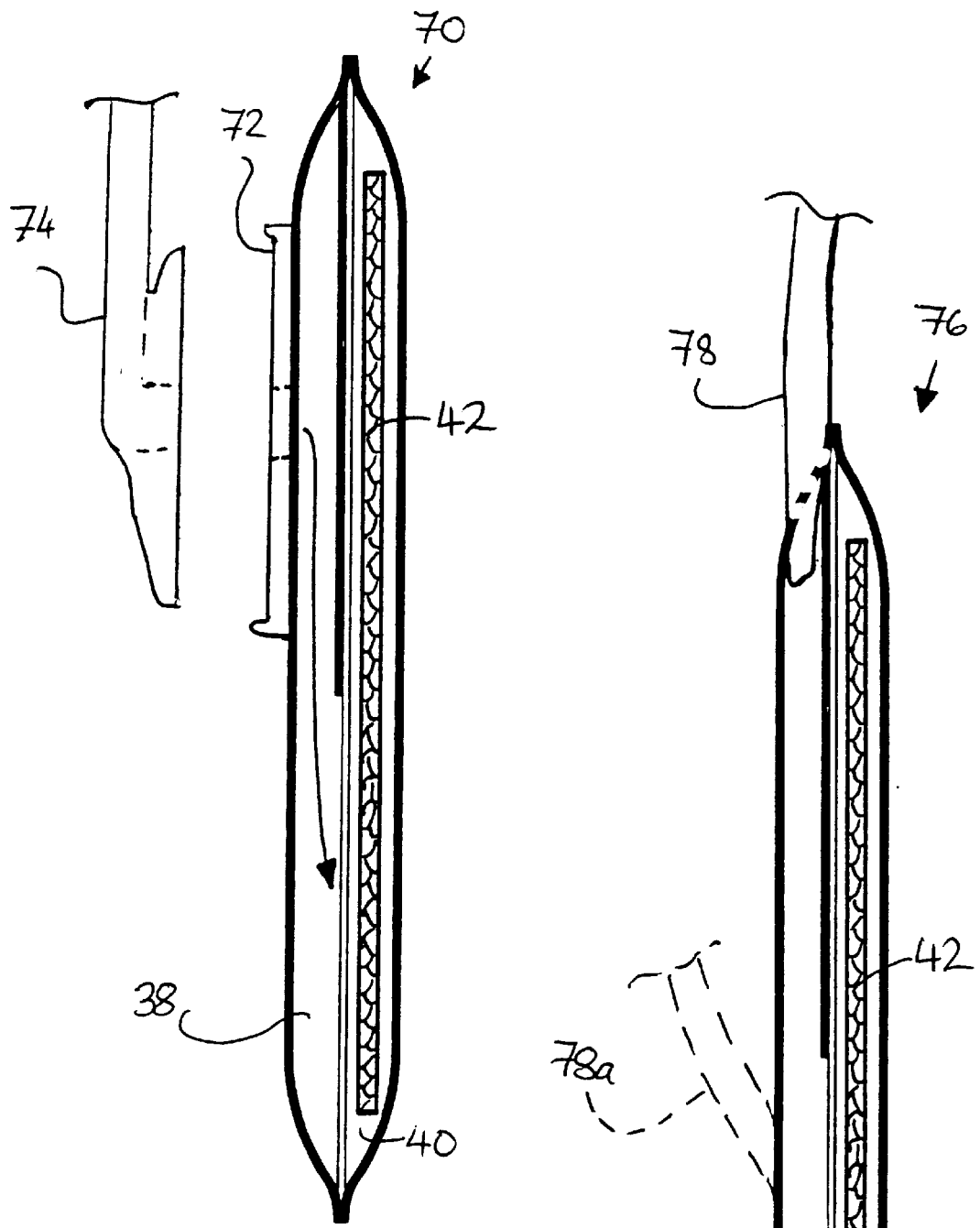
FIG. 6 is a cross-section through an incontinence pouch.
Figure 7:
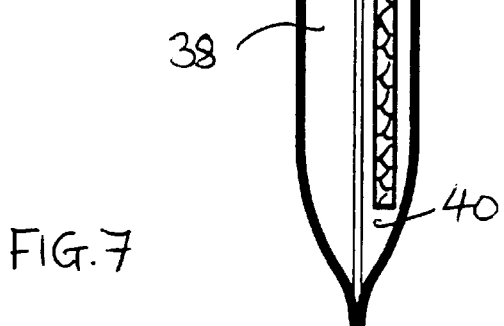
FIG. 7 is a cross-section through an alternative design of incontinence pouch.

For example, FIG. 6 illustrates an incontinence leg-bag pouch 70 having a design very similar to that described above. However, in FIG. 6, the previous body-aperture coupling member 34 is replaced by an inlet connector 72 for face contact with a catheter connector 74. FIG. 7 illustrates an alternative embodiment of incontinence leg-bag pouch 76 having a fixed inlet tube 78 instead of an inlet connector 72.

The invention also provides greater freedom in the design and positioning of the pouch, whether an incontinence pouch or a urostomy pouch, in view of the wicking effect to absorb the urine. The pouch is able to collect urine in a region above the level of the inlet to the pouch. Such an effect has not been possible in any prior art designs. For example, if desired, the inlet tube could enter the incontinence pouch of FIG. 7 at a lower position (as shown in phantom at 78a).

It will be appreciated that the foregoing description is merely illustrative of preferred forms of the invention, and that many modifications may be made using the above described principles. In particular, although the partition 36 provides many advantages, this is not essential in all embodiments of the invention.

Also, although the illustrated embodiments have only two chambers, it will be appreciated that a greater number of chambers may be used if desired. For example, the inlet aperture could then communicate indirectly with the intermediate chamber 38 via one or more additional, upstream, chambers.

The Applicant claims protection any novel feature or idea described herein and/or illustrated in the drawings whether or not emphasis has been placed thereon.

I claim:

1. A pouch for collecting liquid excreted by a body, the pouch comprising:

first and second walls defining a pouch envelope;

a third wall for defining first and second chambers within the envelope and arranged with a portion of one chamber generally horizontally in front of the other when the pouch is in an upright orientation in which it is worn, the third wall including at least a portion thereof of a material porous to liquid;

an entrance aperture communicating directly or indirectly with the first chamber; and a material in the second chamber for gelling liquid contents therein, for storing liquid in the second chamber as a gel;

wherein the gelling material extends above the lower level of the entrance aperture when the pouch is in said upright orientation in which it is worn normally, whereby the gelling material is able to store liquid as a gel in an upper region of the second chamber above said lower level of the entrance aperture;

the third wall being configured to admit liquid from the first chamber to the second chamber, and to obstruct the escape of gel from the second chamber, said third wall including a liquid impermeable portion and a liquid permeable portion.

2. A pouch according to claim 1, wherein the pouch is ventless.

3. A pouch according to claim 2, wherein the pouch is a urine collection pouch.

4. A pouch according to claim 3, wherein the pouch is a urostomy pouch.

5. A pouch according to claim 3, wherein the pouch is an incontinence pouch.

6. A pouch according to claim 1, wherein the third wall comprises at least a portion thereof having directional flow characteristics to admit liquid to flow from the first chamber to the second chamber, but to obstruct the flow of liquid from the second chamber to the first chamber.

7. A pouch according to claim 1, wherein the gelling material has a wicking characteristic able to draw liquid upwardly by a wicking effect.

8. A pouch according to claim 1, wherein the gelling material comprises a superabsorbent material.

9. A pouch according to claim 8, wherein the superabsorbent material comprises an alkali metal polyacrylate.

10. A pouch according to claim 9, wherein the superabsorbent material comprises sodium polyacrylate.

11. A pouch according to claim 8, wherein the superabsorbent material forms part of a composition including glycerol.

12. A pouch according to claim 1, wherein the gelling material is screened from the entrance aperture by a wall or wall portion of liquid impermeable material.

13. A pouch according to claim 1, wherein liquid entering the first chamber from the entrance aperture is guided downwardly and is admitted to the second chamber only at a level lower than the level of the entrance aperture.

14. A pouch according to claim 1 wherein the third wall comprises first and second layers, the first layer being of liquid impermeable material, and the second layer being of liquid permeable material.

15. A pouch according to claim 1, wherein the pouch has an outer profile or a weld seam consisting substantially of a first upper arcuate portion and a second lower arcuate portion, at least one of the arcuate portions having a maximum transverse dimension greater than the transverse dimension at the point where the first and second portions meet.

16. A pouch according to claim 1, wherein the pouch has an outer profile or a weld seam consisting substantially of a first upper arcuate portion and a second lower arcuate portion, at least one of the arcuate portions having a maximum transverse dimension greater than the transverse dimension at the point where the first and second portions meet, and wherein the profile or seam defines a figure-of-eight shape.

17. A pouch according to claim 16, wherein one of the portions has a greater maximum dimension than the other.

18. A pouch according to claim 1, wherein the pouch has an outer profile or a weld seam consisting substantially of a first upper arcuate portion and a second lower arcuate portion, at least one of the arcuate portions having a maximum transverse dimension at the point where the first and second portions meet, and wherein the profile or seam includes a waist at the point where the first and second portions meet.

19. A pouch according to claim 18, wherein at least one of the first and second portions corresponds to an arc of a circle.

20. A pouch according to claim 18, wherein the entrance aperture is positioned generally in register with a centre of curvature of one of the portions.

21. A pouch for collecting liquid excreted by the body, the pouch comprising:

first and second walls defining a pouch envelope;

a third wall for defining first and second chambers within the envelope and arranged with a portion of one chamber generally horizontally in front of the other when the pouch is in an upright orientation in which it is worn, the third wall including at least a portion thereof of a material porous to liquid;

an entrance aperture communicating directly or indirectly with the first chamber; and a material in the second chamber for gelling liquid contents therein, for storing liquid in the second chamber as a gel;

wherein the gelling material extends above the lower level of the entrance aperture when the pouch is in said upright orientation in which it is worn normally, whereby the gelling material is able to store liquid as a gel in an upper region of the second chamber above said lower level of the entrance aperture;

the third wall being configured to admit liquid from the first chamber to the second chamber, and to obstruct the escape of gel from the second chamber, said gelling material having a wicking characteristic able to draw liquid upwardly by a wicking effect.

\* \* \* \* \*